United States Patent [19]

Schwan et al.

[11] 4,349,677

[45] Sep. 14, 1982

[54] 3,4-DIHYDRO-3,4-ISOQUINOLINEDIONE 4-OXIME

[75] Inventors: Thomas J. Schwan; Homer A. Burch; Joseph E. Gray, all of Norwich, N.Y.

[73] Assignee: Morton-Norwich Products, Inc., Norwich, N.Y.

[21] Appl. No.: 319,443

[22] Filed: Nov. 9, 1981

[51] Int. Cl.³ .................. C07D 217/24; A61K 31/47
[52] U.S. Cl. .................................... 546/142; 424/258
[58] Field of Search ........................................ 546/142

[56] References Cited

U.S. PATENT DOCUMENTS 4,150,135  4/1979  Ripka .................................. 546/142

OTHER PUBLICATIONS

Buu-Hoi, et al., "J. Het. Chem." vol. 5 (8), 1968, pp. 545-547.

Primary Examiner—Mary C. Lee
Assistant Examiner—James H. Turnipseed
Attorney, Agent, or Firm—Anthony J. Franze

[57] ABSTRACT

The compound 3,4-dihydro-3,4-isoquinolinedione 4-oxime is useful as an antifungal agent.

1 Claim, No Drawings

3,4-DIHYDRO-3,4-ISOQUINOLINEDIONE 4-OXIME

This invention is concerned with chemical compounds. In particular, it is concerned with the compound 3,4-dihydro-3,4-isoquinolinedione 4-oxime.

This compound is useful as an antifungal agent. For example, when administered perorally by gavage in water to mice systemically infected with *Torulopsis glabrata*, salutary effect is elicited. In a peroral dose of about 35 mg/kg to 50 infected mice a reduction in viable cell count is observed in both spleen and heart organs. Suitable compositions for convenient use of the compound of this invention consist of conventional dosage forms such as solutions, tablets, suspensions and capsules using commonly employed excipients and adjuvants of the pharmaceutical art with which there is no incompatibility.

In order that this invention may be readily available to and understood by those skilled in the art the following now preferred method of making it is set forth:

To a solution of 47.1 g (0.48 mole) of conc. $H_2SO_4$ in 390 ml of water stirred at 30° was added quickly 17.3 g (0.12 mole) of 3-aminoisoquinoline. The solution was cooled to 5° and a solution of 24.8 g (0.36 mole) of sodium nitrite in 60 ml of water was added over 45 min at 5°–10°. The mixture was stirred at 3°–7° for 2.5 hr and the solid was filtered, washed with 2×75 ml of $H_2O$, and dried at 60° to give 20.2 g (88%) of the product. Recrystallization from water gave an analytical sample, m.p. 190°–200° (dec.).

Anal. Calcd. For $C_9H_6N_2O_2.H_2O$: C, 56.25; H, 4.19; N, 14.58; $H_2O$, 9.37. Found: C, 56.02; H, 4.25; N, 14.44; $H_2O$, 10.1.

What is claimed is:

1. The compound 3,4-dihydro-3,4-isoquinolinedione 4-oxime.

* * * * *